(12) United States Patent
Suzuki et al.

(10) Patent No.: US 7,750,053 B2
(45) Date of Patent: *Jul. 6, 2010

(54) COMPOSITIONS AND METHODS FOR ALLEVIATING HYPERTENSION OR PREVENTING A RISE IN BLOOD PRESSURE

(75) Inventors: Atsushi Suzuki, Tochigi (JP); Ryuji Ochiai, Tochigi (JP); Ichiro Tokimitsu, Tochigi (JP)

(73) Assignee: KAO Corporation, Tokyo (JP)

( * ) Notice: Subject to any disclaimer, the term of this patent is extended or adjusted under 35 U.S.C. 154(b) by 181 days.

This patent is subject to a terminal disclaimer.

(21) Appl. No.: 09/922,694

(22) Filed: Aug. 7, 2001

(65) Prior Publication Data

US 2002/0051810 A1 May 2, 2002

(30) Foreign Application Priority Data

Aug. 7, 2000 (JP) .............................. 2000-238039

(51) Int. Cl.
*A01N 33/18* (2006.01)
*A01N 33/00* (2006.01)
(52) U.S. Cl. ...................................... 514/728; 514/730
(58) Field of Classification Search ................. 424/400, 424/439, 464, 489
See application file for complete search history.

(56) References Cited

U.S. PATENT DOCUMENTS

| 4,707,472 | A | | 11/1987 | Inagaki et al. | |
|---|---|---|---|---|---|
| 5,374,441 | A | * | 12/1994 | Gibson et al. ............... | 426/656 |
| 5,932,623 | A | | 8/1999 | Tanabe et al. | |
| 5,955,269 | A | * | 9/1999 | Ghai et al. ...................... | 435/6 |
| 5,958,417 | A | * | 9/1999 | Hsu ........................... | 424/764 |
| 5,994,413 | A | | 11/1999 | Tanabe et al. | |
| 6,120,823 | A | * | 9/2000 | Cirigliano et al. ........... | 426/321 |
| 6,261,565 | B1 | * | 7/2001 | Empie et al. ................. | 424/725 |
| 6,310,100 | B1 | * | 10/2001 | Suzuki et al. ................ | 514/570 |
| 6,423,747 | B1 | * | 7/2002 | Lanzendorfer et al. ...... | 514/456 |
| 2002/0054923 | A1 | * | 5/2002 | Suzuki et al. ................ | 424/729 |
| 2002/0187239 | A1 | * | 12/2002 | Miljkovic et al. ........... | 426/590 |

FOREIGN PATENT DOCUMENTS

| EP | 1 090 635 | | 4/2001 |
|---|---|---|---|
| EP | 1090635 A2 | * | 4/2001 |
| EP | 1186294 A2 | * | 3/2002 |
| EP | 1186297 A2 | * | 3/2002 |
| JP | 4-243822 | | 8/1992 |
| JP | 04243822 A | * | 8/1992 |
| JP | 04-316597 | | 11/1992 |
| JP | 07-285876 | | 10/1995 |
| JP | 8-259453 | | 10/1996 |
| WO | WO 98/01143 | | 1/1998 |

OTHER PUBLICATIONS

Z. Miao, et al Biosci. Biotech. Biochem. vol. 61, No. 3, pp. 527-529, "Synthesis and Biological Activities of Ferulic Acid-Amino Acid Derivatives", 1997.*
Abraham, S. K, Anti-Genotoxic Effects in Mice After the Interaction Between Coffee and Dietary Constituents, 1996, Fd Chem Toxic, vol. 34. No. 1, pp. 15-20.*
Takako Yokozawa,* Jia Jun Zhou and Hikokichi Oura "Effects on Blood Pressure of Caffeic Acid Analogues Isolated from Salviae Miltiorrhizae Radix in Rats with Adenine-induced Renal Hyper tension" Phytotherapy Research, vol. 9, 105-109 (1995).*
Mou-Tuan Huang, Robert C. Smart, Ching-Quo Wong, and Allan H. Conney "Inhibitory Effect of Curcumin, Chlorogenic Acid, Caffeic Acid, and Ferulic Acid on Tumor Promotion in Mouse Skin by 12-O-Tetradecanoylphorbol-13-acetate" [Cancer Research 48, 5941-5946, Nov. 1, 1988].*
Takako Yokozawa et al. "Effects on Blood Pressure of Caffeic Acid Analogues Isolated from Salviae Miltiorrhizae Radix in Rats with Adenine-induced Renal Hyper tension" Phytotherapy Research, vol. 9, 105-109 (1995).*
Kitiyakara et al. "Antioxidants for hypertension" Curr-Opin-Nephrol-Hypertens. Sep. 1998; 7(5): 531-8.*
Joann E. Manson et al. "A Secondary Prevention Trial of Antioxidant Vitamins and Cardiovascular Disease in Women Rationale, Design, and Methods" Ann Epidemiol 1995;5:261-269.*
Antonella Saija et al. "Ferulic and caffeic acids as potential protective agents against photooxidative skin damage" Sci Food Agric 79:476. 480 (1999).*
R. Adams, et ano., "Preparation and Reactions of O-Hydroxycinnamic Acids and Esters", *Journal of American Chemical Society*, Nov. 5, 1952, vol. 74, pp. 5346-5348.
Z. Miao, et al., Biosci. Biotech. Biochem., vol. 61, No. 3, pp. 527-529, "Synthesis and Biological Activities of Ferulic Acid-Amino Acid Derivatives", 1997.
S. K. Abraham, et al., Food and Chemical Toxicology, vol. 34, No. 1, pp. 15-20, XP-001148404, "Anti-Genotoxic Effects in Mice After the Interaction Between Coffee and Dietary Constituents", 1996.
J.- T. Cheng, et al., The Chinese Pharmaceutical Journal, vol. 46, No. 6, pp. 575-582, XP-008007443, "Antihypertensive Activity of Phenolics From the Flower of Lonicera Japonica", 1994.
P. D. Lister, et al., Journal of American Society for Horticultural Science, vol. 111, No. 6, pp. 892-896, "Application of Flavonoid Glycosides and Phenolic Acids to Suppress Firmness Loss in Apples", 1986.
H.- D. Mosel, et al., Zeitschrift fuer Lebensmittel-Untersuchung under-Forschung, vol. 154, No. 1, pp. 6-11, "The Phenolics of Fruits. III. The Content of Catechins and Hydroxycinnamic Acids in Pome and Stone Fruits", 1974.
U.S. Appl. No. 11/209,672, filed Aug. 24, 2005, Suzuki, et al.
U.S. Appl. No. 11/452,374, filed Jun. 14, 2006, Suzuki, et al.
U.S. Appl. No. 11/813,978, filed Jul. 13, 2007, Ochiai, et al.

* cited by examiner

*Primary Examiner*—L Blaine Lankford
*Assistant Examiner*—Thane Underdahl
(74) *Attorney, Agent, or Firm*—Oblon, Spivak, McClelland, Maier & Neustadt, L.L.P.

(57) ABSTRACT

Products and compositions for preventing or reducing the severity of hypertension. These products contain (a) ferulic acid or a ferulate ester, and (b) caffeic acid and/or a chlorogenic acid. The preventive or remedy can suppress a rise in blood pressure and alleviate hypertension, and is usable as a food.

10 Claims, No Drawings

COMPOSITIONS AND METHODS FOR ALLEVIATING HYPERTENSION OR PREVENTING A RISE IN BLOOD PRESSURE

TECHNICAL FIELD

The present invention relates to products and compositions that prevent, remedy or reduce the severity of hypertension and that are capable of suppressing a rise in blood pressure.

BACKGROUND ART

Hypertension in Japan ranks first among reasons why patients attend hospitals. According to the National Life Fundamental Survey of Ministry of Health and Welfare (fiscal 1998), in Japan, 64 patients per 1000 were admitted to hospitals for hypertension.

Heart diseases such as angina pectoris, myocardial infarction and heart failure and cerebrovascular diseases such as cerebral infarction, cerebral hemorrhage and subarachnoid hemorrhage are closely related to hypertension and rank second and third, respectively, among the causes of death of the Japanese.

Hypertension may be treated by the administration of blood-pressure lowering pharmaceuticals such as diuretics, sympathetic inhibitors, vasodilators or angiotensin-converting enzyme inhibitors. Such drugs are mainly applied to patients suffering from severe hypertension. Although many of the pharmaceuticals administered to treat hypertension are satisfactory in their effectiveness, significant side-effects such as tachycardia and bradycardia can be a serious burden for patients.

Hypertension, especially its milder forms, may also be treated by generally improving lifestyle, such as through dietetic therapy, kinesitherapy and limitation of alcoholic intake or smoking. The importance of such changes in lifestyle is now being increasingly recognized and appreciated, not only for milder forms of hypertension, but also for more severe cases.

Above all, improvement of eating habits has received great attention. There exist a large number of foods, which have traditionally been said to have blood pressure lowering action. Food products have been briskly searched in order to identify and isolate components that lower blood pressure.

It has been reported that phenols such as caffeic acid contained crude form in the spike of *Schizonepeta tenuifolia* Briq. exerts calcium antagonism and may be useful for the treatment of vascular diseases such as hypertension (Japanese Patent Application Laid-Open (Kokai) No. Hei 4-243822).

The use of the juice of an unripe fruit such as apples, pears, peaches or similar fruits belonging to the family Rosaceae has also been proposed as a hypotensor. Such juice contains, as polyphenols, caffeic acid and chlorogenic acid having angiotensin I converting enzyme (ACE) inhibitory action (Japanese Patent Application Laid-Open (Kokai) No. Hei 8-259453.

However, foods which are said to be effective for lowering blood pressure or their effective ingredients are not always satisfactory in their effectiveness and many of them do not start to exert significant blood pressure reducing effects immediately after intake or exert long-last anti-hypertensive effects.

Therefore, one object of the present invention is to provide a preventive or remedy for hypertension which has excellent safety, does not become a burden for patients even by daily intake, has higher antihypertensive action and exerts significant prompt and/or long-lasting antihypertensive effects.

DISCLOSURE OF THE INVENTION

The present inventors have found that a combination of ferulic acid (or an ester thereof), and caffeic acid and/or chlorogenic acid exerts prompt blood pressure lowering effects and, by prolonged administration, suppresses rises in blood pressure. This combination of ingredients also has reduced side effects such as bradycardia.

The chemical structures of caffeic acid, one type of a chlorogenic acid, and ferulic acid are shown below:

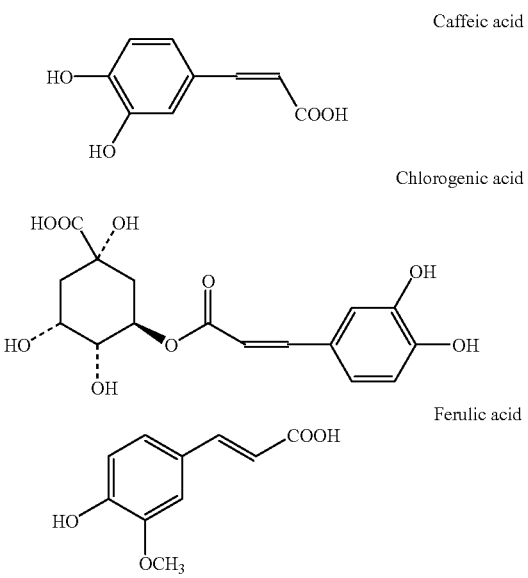

The present invention thus provides products and compositions for the prevention, alleviation or reduction of hypertension. These compositions comprise the following components (a) and (b):

(a) a component selected from ferulic acid, an ester thereof or a pharmaceutically acceptable salt thereof, and (b) a component selected from caffeic acid or a chlorogenic acid, or a pharmaceutically acceptable salt thereof.

Another aspect of the present invention, provides a food containing or supplemented to contain the above-described components (a) and (b).

A further aspect of the present invention provides the use of the above-described components (a) and (b) for the preparation of a product that prevents, treats, reduces or remedies hypertension.

A still further aspect of the present invention provides a method for treating hypertension that comprises the administration of an effective amount of the above-described components (a) and (b).

A further aspect of the invention is a method for providing prompt blood pressure reduction by the administration of a composition comprising ferulic acid, an ester thereof, or a pharmaceutically acceptable salt thereof.

A still further aspect of the invention is a method for providing long-lasting blood pressure reduction by administering a composition comprising caffeic acid or a chlorogenic acid.

BEST MODE FOR CARRYING OUT THE INVENTION

The ferulic acid or ester thereof as component (a) to be used in the present invention can be obtained by either extraction from a natural substance, particularly, a plant which contains it, or by its industrial preparation, for instance, by chemical synthesis.

Preferred examples of plants containing ferulic acid or esters of ferulic acid include coffee, onion, Japanese radish, lemon, *Angelicae radix, Cnidii Rhizoma*, goldthread, asafetida, sugarcane, corn, barley and rice, with rice being particularly preferred. The term "rice" as used herein means raw or dry seeds of rice (*Oryza sativa* LINNE).

Esters of ferulic acid include those obtained by conversion upon extraction or fractionation of those originally contained in a natural substance, particularly, a plant; and to the chemically modified products thereof. For example, rice bran oil obtained from rice bran is separated using hydrous ethanol and hexane at room temperature under a weak alkaline condition and ferulate ester is available in the hydrous ethanol fraction. Ferulic acid can be obtained by hot hydrolysis of the ferulate ester obtained in the above-described manner with sulfuric acid under pressure, followed by purification. It can also be obtained by culturing bacteria (Pseudomonas) in a broth containing a clove oil obtained by steam distillation of buds and leaves of *Syzygium aromaticum* MERRILL et PERRY or a broth containing eugenol available by purification of the clove oil, followed by separation of the resulting culture broth and purification. Chemical synthesis of ferulic acid is attained, for example, by condensation reaction of vanillin and malonic acid, Journal of American Chemical Society, 74: 5346 (1952). Ferulic acid has steric isomers. Any one of them is usable. A mixture of the isomers is also usable.

As the alcohol moiety of the ferulate ester to be used in the present invention, $C_{1-40}$ alcohols are preferred. Examples include linear or branched alkyl or alkenyl alcohols, aryl alcohols, monoterpene alcohols, sesquiterpene alcohols, diterpene alcohols, triterpene alcohols, sterols, and trimethyl sterols, more specifically, ethanol, oleyl alcohol, 2-ethylhexyl alcohol, allyl alcohol, cetyl alcohol, menthyl alcohol, phenol, benzyl alcohol, cholesterol, cycloartenol, 24-methylene cycloartenol, campesterol, β-sitosterol, cycloartanol, cycloprenol, α-sitosterol, stigmasterol, stigmastanol, α-sitostanol, β-sitostanol and campestanol.

Ferulic acid has improved water solubility and increased physiological availability when it is in the form of a salt. No particular limitation is imposed on the salt of the ferulic acid insofar as it is pharmaceutically acceptable. Examples of a basic substance for the formation of such a salt include hydroxides of an alkali metal such as lithium hydroxide, sodium hydroxide and potassium hydroxide, hydroxides of an alkaline earth metal such as magnesium hydroxide and calcium hydroxide, inorganic bases such as ammonium hydroxide and basic amino acids such as arginine, lysine, histidine and ornithine, and organic bases such as monoethanolamine, diethanolamine and triethanolamine. Out of them, hydroxides of an alkali metal or alkaline earth metal are particularly preferred. As a preventive or remedy for hypertension according to the present invention, such a salt, which has been prepared in advance, may be added to a composition composed of the other components, or ferulic acid and a salt-forming component therewith may be added to the composition separately to form their salt therein.

As Component (a), at least two forms of ferulic acid or a ferulic acid derivative or salt may be used in combination. It is preferred for an adult (weight: 60 kg) to take Component (a) in an amount of about 0.001 to about 10 g, preferably about 0.005 to about 5 g, more preferably about 0.01 to about 0.5 g a day.

The caffeic acid or chlorogenic acid to be used as Component (b) in the present invention can be obtained by extraction from a natural substance, particularly, a plant containing these substances, or by industrially preparation, for instance, by chemical synthesis. Examples of the chlorogenic acid to be used in the present invention include neochlorogenic acid, isochlorogenic acids (such as 3,5-dicaffeoylquinic acid), cryptochlorogenic acid, feruloylquinic acid and 5-caffeoylquinic acid. Component (b) may be an extract of a plant abundant in chlorogenic acid such as raw coffee beans, leaves of a nandina and unripe apple fruits, or alternatively, an extract of raw coffee beans available by extraction of the seeds of *Coffea arabica* LINNE with an aqueous solution of ascorbic acid or citric acid under warming.

The caffeic acid and chlorogenic acid products forming Component (b), like those of ferulic acid, have improved water solubility and increased physiological availability when they are in the form of a pharmaceutically acceptable salt. As the salt as component (b), those exemplified above as the salts of ferulic acid can be mentioned. It is preferred for an adult (weight: 60 kg) to take Component (b) in an amount of about 0.001 to about 10 g, more preferably about 0.005 to about 5 g a day.

As Component (b), at least two derivatives or salts of a chlorogenic acid or a caffeic acid product may be used in combination.

The preventive or remedy for hypertension according to the present invention can be formed into an orally administrable or parenterally administrable composition by adding to its effective ingredient a pharmaceutically acceptable carrier. Examples of the orally administrable composition include tablets, granules, fine subtilaes, pills, powders, capsules (hard capsules and soft capsules), troches, chewables and liquids (medical drinks). Examples of the parenterally administrable composition include intravenously administrable preparations such as isotonic, sterile solutions for injection, suppositories and dermatologic preparations for external use.

The compositions for preventing or treating hypertension or high blood pressure according to the present invention have a high degree of safety so that no problem occurs even if those who have a normal blood pressure usually take it as a food. Examples of such compositions in the form of food or beverage include beverages such as juice and coffee, liquid foods such as soup, emulsion or pasty foods such as milk and curry, semi-solid foods such as jelly and gummy; solid foods such as gum, tofu and supplement; powdery foods; and oil or fat containing foods such as margarine, mayonnaise and dressing.

The weight ratio of Component (a) to Component (B) in a combined preparation, that is, Component (a)/(b) preferably ranges from about 0.01 to 50, more preferably ranges from about 0.01 to 5. The weight ratio of Component (a) to Component (b) is confirmed by high-performance liquid chromatography equipped with an electrochemical detector.

It is preferred for an adult (weight: 60 kg) to take the preventive or remedy for hypertension according to the present invention so that the total amount of Components (a) and (b), the effective ingredients, would be about 0.001 to about 20 g, particularly about 0.005 to about 10 g a day. When a plant extract is employed, it is preferred to take it in an amount in terms of a dry weight.

In addition to the combined preparations of the present invention comprising ferulic acid and caffeic acid and/or a chlorogenic acid, compositions comprising any of these ingredients may be formulated to decrease the effects of hypertension or reduce high blood pressure.

Foods or beverages associated with hypertension may advantageously be supplemented with caffeic acid, a chlorogenic acid and/or ferulic acid in dosages that preferably inhibit or reduce the hypertensive effects of the food or beverage. For instance, beverages containing caffeine, such as coffee, have been associated with hypertension and may be supplemented with amounts of caffeic acid, chlorogenic acid and/or ferulic acid to reduce hypertensive effects associated with the consumption of these beverages.

Caffeic acid, a chlorogenic acid and/or ferulic acid may also be compounded as food or nutritional supplements in amounts which preferably reduce hypertension. For instance, these substances may be admixed with a pharmaceutically acceptable excipient, filler or carrier. As such, they may be placed in tablet or capsule form, or compounded in standardized dosages in solid or liquid form.

Breeding or engineering of agricultural products to contain or express higher amounts of caffeic acid, chlorogenic acid and/or ferulic acid may be done so as to obtain products that exert beneficial effects in hypertensive subjects.

EXAMPLES

Example 1

Evaluation of blood pressure reduction (1) Animals provided for test

Prior to initiation of the experimental studies in order to accustom the test animals to sphygmomanometric operation the blood pressure of each test animal—male, 15 week-old, spontaneously hypertensive rats ("SHR")—was preliminarily measured for 7 successive days using a commercially available noninvasive sphygmomanometer for rats (manufactured by Softlon Co., Ltd.).

Rats were all bred in a breeding room in a rat region under uniform conditions at a room temperature at 25±1° C., humidity of 55±10% RH and illumination for 12 hours (from 7:00 am to 7:00 pm).

(b) Administration method and amount

In the control group (Control Plot, see Table 1), physiological saline was employed. As a material to be administered, a solution obtained by dissolving 0.2 wt. % (which will hereinafter be simply described as %) of caffeic acid in physiological saline, a solution obtained by dissolving 0.2% of a chlorogenic acid in physiological saline, a solution obtained by dissolving 0.2% of ferulic acid in physiological saline and a solution obtained by dissolving 0.1% of caffeic acid and 0.1% of ferulic acid in physiological saline were used in Test plot 1, Test plot 2, Test plot 3 and Test plot 4, respectively. In Test plot 5, a solution obtained by dissolving 0.1% of a chlorogenic acid and 0.1% of ferulic acid in physiological saline was used, while in Test plot 6, a solution obtained by dissolving 0.05% of caffeic acid, 0.05% of a chlorogenic acid and 0.1% of ferulic acid in physiological saline was used. Each of them was administered from the common carotid artery. The dosage was 1 mL/kg.

(c) Test method

SHRs were fasted overnight and employed for each test group, each group consisted of 5 rats. Systolic blood pressures of the caudal artery prior to intravenous administration, and 10 minutes and 1 hour each after administration were measured.

(4) Statistical treatment method

In Table 1, the changing ratio (%) in systolic blood pressure for each experimental group is reported by its mean value (%) and by its standard deviation. The Student's t-test was used to indicate the statistical significance of the experimental data. A significance level of 5% or less is indicated as "*" in Table 1, and significance level of 0.1% or less as "***".

A lowering ratio of the systolic blood pressure of each of 10 minutes and 1 hour after administration to the systolic blood pressure prior to administration is shown in Table 1. As is apparent from Table 1, the compositions of the present invention induced prompt and/or long-lasting antihypertensive effects and reductions in blood pressure.

TABLE 1

| | | Systolic blood pressure (changing ratio %) | |
|---|---|---|---|
| | | after 10 minutes | After 1 hour |
| Control plot | saline | −1.6 ± 0.6 | −1.9 ± 1.4 |
| Test plot 1 | Caffeic acid (CA) | −4.1 ± 2.1 | −10.2 ± 0.5*** |
| Test plot 2 | Chlorogenic acid (CHA) | −3.2 ± 2.6 | −7.2 ± 1.7* |
| Test plot 3 | Ferulic acid (FA) | −7.8 ± 0.8*** | 0.7 ± 2.6 |
| Test plot 4 | CA + FA | −10.4 ± 1.8*** | −11.3 ± 1.3 *** |
| Test plot 5 | CHA + FA | −9.6 ± 2.2*** | −10.9 ± 0.8 *** |
| Test plot 6 | CA + CHA + FA | −11.1 ± 1.9*** | −13.6 ± 3.4 *** |

*,***A significance level was 5% or less and 0.1% or less, respectively relative to the control group, meaning existence of a significant difference.

Indicated is a mean value ± standard deviation

Example 2

Inhibition of Blood Pressure Rise (1) Test Animals

Under similar conditions to Example 1, male, 6 week old spontaneously hypertensive rats (SHR) were bred.

(2) Administration method and amount

In the Control Plot, test animals were maintained on commercially available powdery feed and drinking water ad libitum.

In Test plot 1, they were maintained ad libitum on drinking water having 0.2% of sodium caffeinate added thereto and commercially available powdery feed having, incorporated therein, 1% of a triterpenol-ferulate ester mixture extracted from rice bran;

In Test Plot 2, on drinking water having 0.2% of a chlorogenic acid and commercially available powdery feed having, incorporated therein, 1% of a ferulic acid and cycloartenol ferulate;

In Test Plot 3, on drinking water having, added thereto, 0.2% of caffeic acid, 1% of a chlorogenic acid and 0.04% of ferulic acid.

(3) Test method

SHRs were employed for the test in groups, each group consisting of 6 rats. Systolic pressure of the caudal artery 4 weeks after administration was measured and the results were treated statistically in a similar manner to Example 1.

Systolic blood pressures prior to administration and 4 weeks after administration are shown in Table 20 Table 2 shows that the according to the present invention exert a marked inhibitory action against blood pressure rise.

TABLE 2

| | | Systolic blood pressure (mmHg) | |
| --- | --- | --- | --- |
| | | Prior to administration | 4 weeks after administration |
| Control plot | Water | 152.1 ± 4.4 | 201.0 ± 3.9 |
| Test plot 1 | Na Caffeinate, triterpenol ferulate ester | 155.3 ± 3.7 | 183.5 ± 4.0* |
| Test plot 2 | Chlorogenic acid, ferulic acid, cycloartenol ferulate | 153.0 ± 5.2 | 181.9 ± 5.3* |
| Test plot 3 | Caffeic acid, chlorogenic acid, ferulic acid | 155.0 ± 4.1 | 188.2 ± 3.4* |

*The significance level relative to the control plot was 5% or less, indicating a significant lowering of the systolic blood pressure of groups treated with the compositions of the present invention.
Indicated is each mean ± standard deviation.

Example 3

Soft Capsules

| | |
| --- | --- |
| Gelatin | 70.0% |
| Glycerin | 22.9 |
| Methyl paraoxybenzoate | 0.15 |
| Propyl paraoxybenzoate | 0.51 |
| Water | 6.44 |

Soft, oval-type capsules having a weight of 150 mg and composed of the above-described composition were filled in a manner known per se in the art with 400 mg of soybean oil, 50 mg of caffeic acid and 50 mg of ferulic acid. These capsules when administered to test subjects exhibit good blood pressure lowering action.

Example 4

Beverage

A beverage according to the present invention was prepared by combining the ingredients enumerated below.

| | |
| --- | --- |
| Skim milk | 3.5% |
| Enzyme-hydrolyzed milk casein | 3.5 |
| Fructose | 9.0 |
| Chlorogenic acid | 0.1 |
| Sodium ferulate | 10.0 |
| Citric acid | 0.1 |
| Ascorbic acid | 0.1 |
| Flavor | 0.1 |
| Water | 73.6 |

It has been found that the beverage having the above-described composition had high storage stability and had good taste.

Example 5

Wheat Flour Products

Wheat flour products according to the present invention were prepared by the combination of the following ingredients:

| | |
| --- | --- |
| Rapeseed oil | 15 g |
| Corn starch | 15 |
| Wheat flour | 42.6 |
| Butter | 5 |
| Fructose | 14 |
| Ferulic acid | 2 |
| Cycloartenol ferulate | 0.4 |
| Table salt | 0.5 |
| Sodium bicarbonate | 0.5 |
| Water | 5 |

Cookies having the above-described composition were baked.

Modifications and other embodiments

Various modifications and variations of the described antihypertensive products, compositions and methods, as well as the concept of the invention will be apparent to those skilled in the art without departing from the scope and spirit of the invention. Although the invention has been described in connection with specific preferred embodiments, it should be understood that the invention as claimed is not intended to be limited to such specific embodiments. Various modifications of the described modes for carrying out the invention which are obvious to those skilled in the medical, biological, chemical or pharmacological arts or related fields are intended to be within the scope of the following claims.

Incorporation by Reference

Each document, patent application or patent publication cited by or referred to in this disclosure is incorporated by reference in its entirety. Any patent document to which this application claims priority is also incorporated by reference in its entirety. Specifically, priority document JP, 2000-238039, filed Aug. 7, 2000 is hereby incorporated by reference.

The invention claimed is:

1. A composition consisting of:
   (a) isolated or purified ferulic acid or an ester thereof, or a pharmaceutically acceptable salt thereof, and
   (b) isolated or purified caffeic acid and/or chlorogenic acid, or pharmaceutically acceptable salts thereof, and
   a suitable excipient or carrier;
   wherein (a) and (b) are present in an amount sufficient to lower blood pressure or suppress a rise in blood pressure when administered to a mammal.

2. The composition of claim 1 in the form of a tablet, granule, fine subtilae, pill, powder, capsule, troche, medicinal drink, solution for injection, suppository, or dermatological preparation.

3. The composition of claim 1, wherein (b) consists of caffeic acid or a pharmaceutically acceptable salt thereof.

4. The composition of claim 1, wherein (b) consists of chlorogenic acid, or a pharmaceutically acceptable salt thereof.

5. The composition of claim 1, wherein (b) consists of caffeic acid and chlorogenic acid, or pharmaceutically acceptable salts thereof.

6. A process for treating hypertension or high blood pressure comprising administering an effective dose of the composition of claim 1 to a subject in need thereof;
 wherein said hypertension is characterized by high systolic or diastolic blood pressure, or both.

7. The process of claim 6, wherein systolic blood pressure is reduced.

8. The process of claim 6, wherein diastolic blood pressure is reduced.

9. The composition of claim 1, wherein the amount of (a) ranges between 0.001 and 10 g, and the amount of (b) ranges from 0.001 and 10 g.

10. The composition of claim 1, wherein the amount of (a) ranges between 0.01 and 0.5 g, and the amount of (b) ranges from 0.01 and 0.5 g.

* * * * *